US011001885B2

(12) United States Patent
Chiou et al.

(10) Patent No.: US 11,001,885 B2
(45) Date of Patent: May 11, 2021

(54) APPARATUS FOR SINGLE MOLECULAR SEQUENCING AND METHOD OF SEQUENCING NUCLEIC ACID MOLECULES

(71) Applicant: Personal Genomics Taiwan, Inc., Hsinchu County (TW)

(72) Inventors: Chung-Fan Chiou, Hsinchu County (TW); Chao-Chi Pan, Hsinchu (TW); Ching-Wei Tsai, Taoyuan (TW); Bor-Huah Chen, Taichung (TW); Jian-Hao Ciou, Changhua County (TW)

(73) Assignee: Personal Genomics Taiwan, Inc., Hsinchu County (TW)

(*) Notice: Subject to any disclaimer, the term of this patent is extended or adjusted under 35 U.S.C. 154(b) by 225 days.

(21) Appl. No.: 16/005,699

(22) Filed: Jun. 12, 2018

(65) Prior Publication Data
US 2018/0355422 A1    Dec. 13, 2018

Related U.S. Application Data

(60) Provisional application No. 62/518,620, filed on Jun. 13, 2017.

(51) Int. Cl.
| | | |
|---|---|---|
| C12Q 1/6869 | (2018.01) | |
| C12Q 1/6876 | (2018.01) | |
| C12Q 1/6874 | (2018.01) | |
| C07H 21/04 | (2006.01) | |
| B01L 3/00 | (2006.01) | |
| B01J 19/00 | (2006.01) | |

(52) U.S. Cl.
CPC ........ *C12Q 1/6869* (2013.01); *B01J 19/0046* (2013.01); *B01L 3/5082* (2013.01); *B01L 3/5085* (2013.01); *B01L 3/50857* (2013.01); *C07H 21/04* (2013.01); *C12Q 1/6874* (2013.01); *C12Q 1/6876* (2013.01); *B01J 2219/00317* (2013.01); *B01J 2219/00511* (2013.01); *B01J 2219/00722* (2013.01); *B01L 2300/0896* (2013.01); *B01L 2300/16* (2013.01); *C12Q 2521/101* (2013.01); *C12Q 2521/525* (2013.01); *C12Q 2525/186* (2013.01); *C12Q 2531/125* (2013.01); *C12Q 2563/107* (2013.01); *C12Q 2563/159* (2013.01)

(58) Field of Classification Search
CPC .. C12Q 1/6869; C12Q 1/6874; C12Q 1/6876; B01L 3/5085
See application file for complete search history.

(56) References Cited

U.S. PATENT DOCUMENTS

| | | |
|---|---|---|
| 6,762,048 B2 | 7/2004 | Williams |
| 8,481,264 B2 | 7/2013 | Bjornson et al. |
| 8,603,741 B2 | 12/2013 | Emig et al. |
| 8,906,831 B2 * | 12/2014 | Eid ................. G01N 33/54313 506/16 |
| 2003/0174992 A1 | 9/2003 | Levene et al. |
| 2010/0075328 A1 | 3/2010 | Bjornson et al. |
| 2010/0311061 A1 | 12/2010 | Korlach et al. |
| 2011/0223590 A1 | 9/2011 | Chiou et al. |
| 2014/0295412 A1 | 10/2014 | Huang |
| 2015/0141266 A1 | 5/2015 | Turner et al. |

FOREIGN PATENT DOCUMENTS

| | | | |
|---|---|---|---|
| JP | 2013522605 | 6/2013 | |
| JP | 2015519911 | 7/2015 | |
| JP | 2016065878 | 4/2016 | |
| WO | WO-2004070007 A2 * | 8/2004 | ........... C12Q 1/6834 |
| WO | 2010027497 | 3/2010 | |
| WO | 2016075204 | 5/2016 | |

OTHER PUBLICATIONS

Syvanen, Ann-Christine, From Gels to Chips: "Minisequencing" Primer Extension for Analysis of Point Mutations and Single Nucleotide Polymorphisms, Human Mutation, 13:1-10 (1999). (Year: 1999).*
T. D. Harris et al., "Single-Molecule DNA Sequencing of a Viral Genome", Science, vol. 320, Apr. 4, 2008, pp. 106-109.
Rhoads Anthony et al., "PacBio Sequencing and Its Applications", Genomics Proteomics and Bioinformatics, vol. 13, No. 5, Nov. 2, 2015, pp. 278-289.
"Search Report of Europe Counterpart Application", dated Aug. 10, 2018, p. 1-p. 8.
John Eid et al., "Real-time DNA sequencing from single polymerase molecules", Science, Jan. 2009, pp. 133-138.
Sara Goodwin et al., "Coming of age: ten years of next-generation sequencing technologies", Nature Reviews Genetics, Jun. 2016, pp. 333-351.

* cited by examiner

*Primary Examiner* — Angela M. Bertagna
*Assistant Examiner* — Carolyn L Greene
(74) *Attorney, Agent, or Firm* — JCIPRNET

(57) ABSTRACT

An apparatus suitable for single molecule sequencing. The apparatus includes at least one nanowell, a plurality of nucleic acid immobilization moieties, and a plurality of types of nucleic acid fragments. The nanowell has an observation zone. The nucleic acid immobilization moieties are disposed in or proximate to the observation zone. The nucleic acid fragments are immobilized to the nucleic acid immobilization moieties, respectively. At least one polymerase is disposed in the observation zone. A method of sequencing nucleic acid molecules using the above-mentioned apparatus is provided.

13 Claims, 6 Drawing Sheets

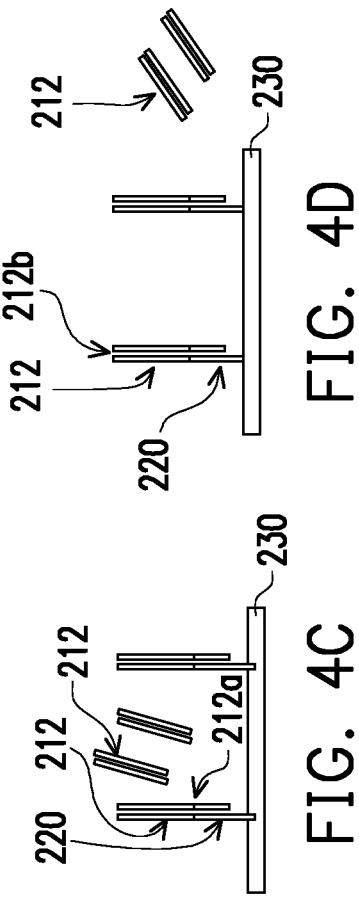
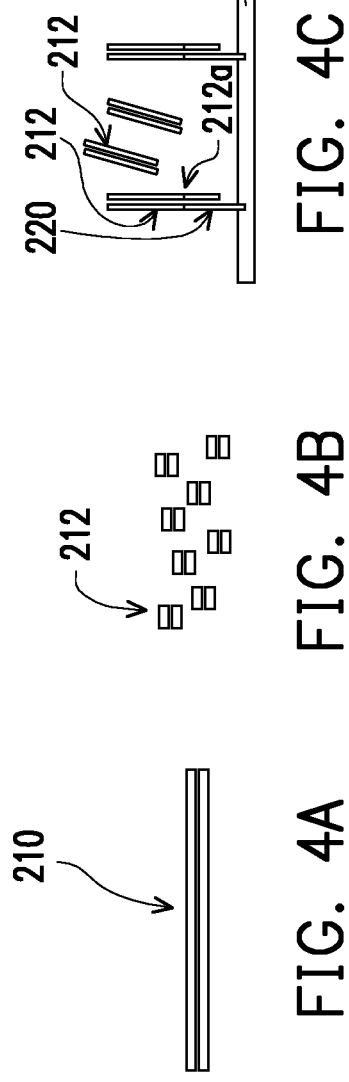
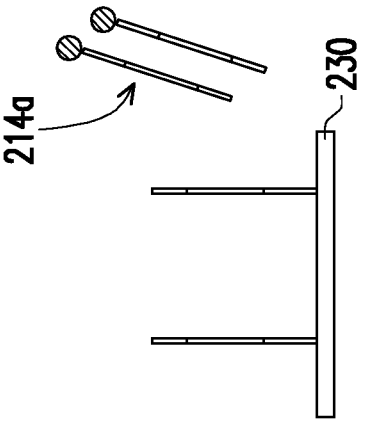
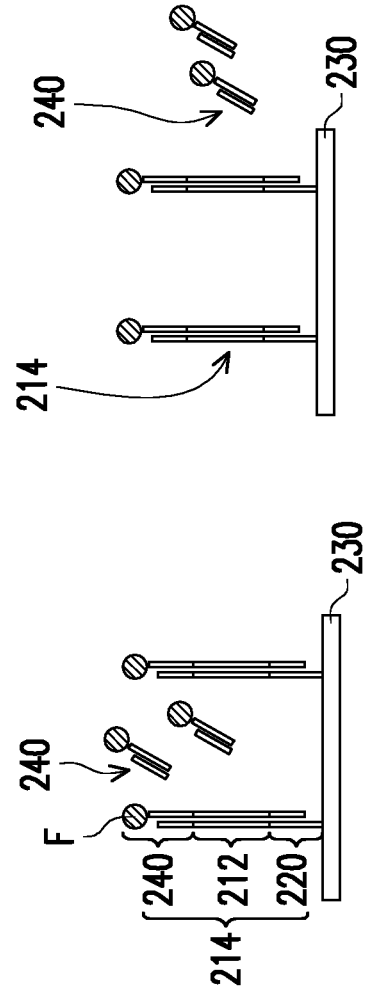

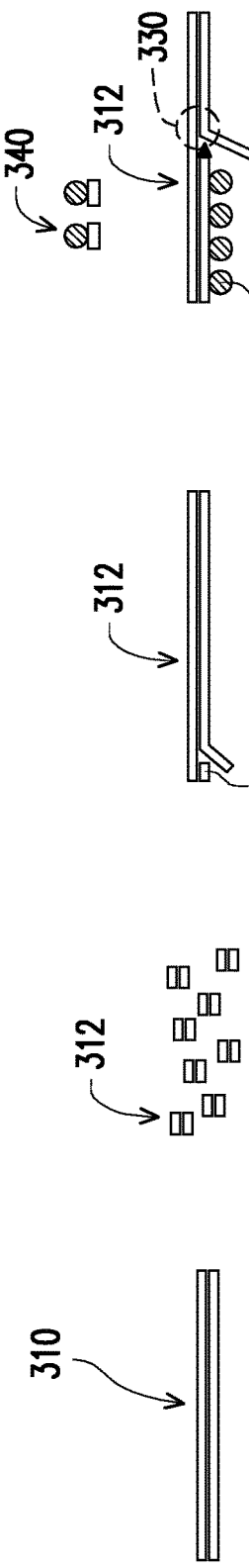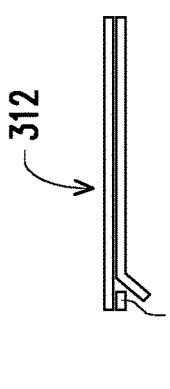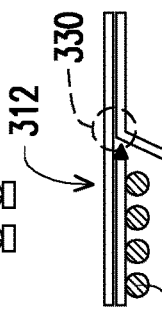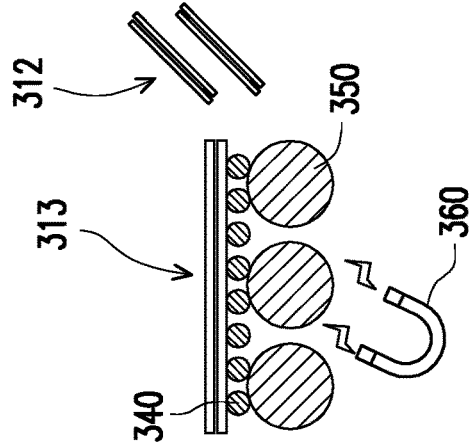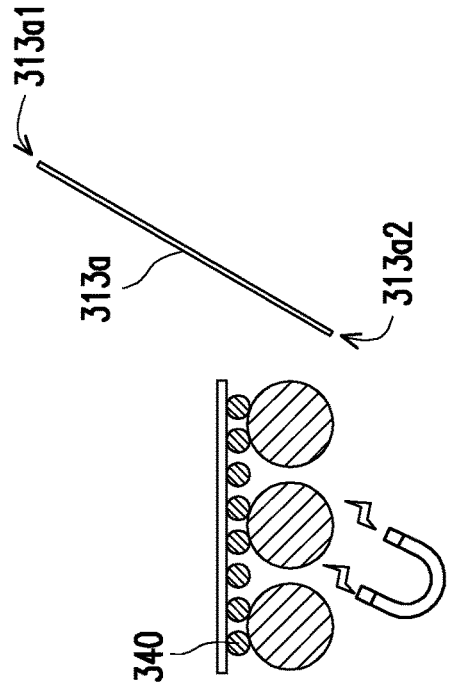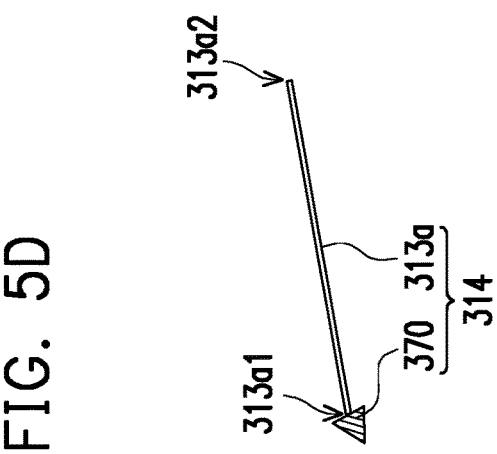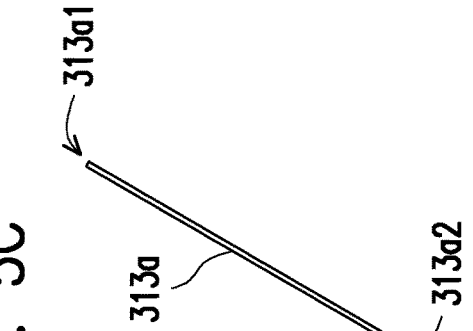

APPARATUS FOR SINGLE MOLECULAR SEQUENCING AND METHOD OF SEQUENCING NUCLEIC ACID MOLECULES

CROSS REFERENCE TO RELATED APPLICATION

This application claims the priority benefit of U.S. provisional application Ser. No. 62/518,620, filed on Jun. 13, 2017. The entirety of the above-mentioned patent application is hereby incorporated by reference herein and made a part of specification.

BACKGROUND

Technical Field

The invention relates to an apparatus and a method for sequencing, and more particularly, to an apparatus for single molecule sequencing and a method of sequencing nucleic acid molecules.

Description of Related Art

Conventional strategies for single molecule sequencing-by-synthesis immobilize one polymerase or one template within or proximal to a reaction region within one observation space. One of the current single molecule sequencing methods includes the following steps. A nucleic acid template (such as DNA or RNA) to be sequenced forms a closed loop (circular template).

Then, the nucleic acid template is captured by the polymerase immobilized inside the detectable zone, with its properties of strand displacement activity and high processivity. After that, the sequence of the template is read several times via single molecule sequencing-by-synthesis (SBS) process. In this method, the final sequencing result is determined by the statistical consensus of useful redundant reads. However, the method requires polymerase with strand displacement activity and high processivity, and once the polymerase losses of activity or releases the nucleic acid template, the sequencing is terminated. The method also requires very precise loading process to maintain one template and allow only one template in each detectable zone, so that those detectable zones having no template or having more than one templates would be considered as failure sites. The strict requirement thus narrows the operation window.

SUMMARY

The present invention provides an apparatus suitable for single molecule sequencing with the advantages of high throughput and reduced sample preparation time.

The present invention provides a method of sequencing nucleic acid molecules by using the above-mentioned apparatus.

The present invention provides an apparatus suitable for single molecule sequencing. The apparatus includes at least one nanowell, a plurality of nucleic acid immobilization moieties, a plurality of types of nucleic acid fragments, and at least one polymerase. The nanowell has an observation zone. The nucleic acid immobilization moieties are disposed in or proximate to the observation zone. The nucleic acid fragments are immobilized to the nucleic acid immobilization moieties, respectively. The polymerase is disposed in the observation zone.

In an embodiment of the invention, a diameter of the observation zone ranges from 10 nm to 500 nm, and a height of the observation zone is less than 200 nm.

In an embodiment of the invention, the plurality of types of nucleic acid fragments are linear.

In an embodiment of the invention, the plurality of types of nucleic acid fragments include 50 nucleotides to 200 nucleotides in length.

In an embodiment of the invention, the at least one polymerase is one polymerase.

In an embodiment of the invention, the nucleic acid fragments include more than 200 nucleotides in length.

In an embodiment of the invention, the at least one polymerase includes a plurality of polymerases and the apparatus further includes a plurality of polymerase immobilization moieties. The polymerase immobilization moieties are disposed in the observation zone and the polymerases are immobilized to the polymerase immobilization moieties.

The present invention provides a method of sequencing nucleic acid molecules and includes the following steps. (a) At least one nanowell is provided, wherein the nanowell has an observation zone. (b) A plurality of types of nucleic acid fragments are immobilized to the observation zone through a plurality of nucleic acid immobilization moieties. (c) One primer and a plurality of labelled nucleotide analogs are provided into the nanowell, wherein the primer and one of the nucleic acid fragments form a primer-nucleic acid fragment complex in the observation zone. (d) A nascent strand is formed by initiating a nascent strand synthesizing reaction of the primer-nucleic acid fragment complex through using a polymerase and incorporating the labelled nucleotide analogs into the primer-nucleic acid fragment complex. (e) The sequence of the nucleic acid fragments is determined by detecting the incorporated sequence of the labelled nucleotide analogs.

In an embodiment of the invention, the method further includes the following steps. (f) The nascent strand is dissociated. (g) Step (c) to step (f) are repeated.

In an embodiment of the invention, step (c) further includes adding the polymerase.

In an embodiment of the invention, the method further includes the following steps. A plurality of polymerases are immobilized to the observation zone through a plurality of polymerase immobilization moieties, wherein the polymerase used in step (d) is one of the plurality of polymerases.

In an embodiment of the invention, the step of immobilizing the plurality of polymerases is performed before step (c).

In an embodiment of the invention, the method further includes the following steps. (f) The nascent strand is dissociated. (g) Step (c) to step (f) are repeated, wherein the polymerase used in repeated step (d) is one of the plurality of polymerases.

In an embodiment of the invention, a preparing method of the plurality of types of nucleic acid fragments includes the following steps. An extracted genomic DNA is provided. The extracted genomic DNA is fragmented into a plurality of DNA fragments. One end of the DNA fragments is joined onto dsDNA adaptors, wherein the dsDNA adaptors are immobilized on a solid phase. Labelled adaptors are joined onto the other end of the DNA fragments to form labelled DNA fragments. A plurality of single-strand DNA fragments are eluted by dissociating the labelled DNA fragments.

In an embodiment of the invention, before joining the labelled adaptors and before eluting the plurality of single-strand DNA fragments further includes performing a washing process, respectively.

In an embodiment of the invention, a preparing method of the plurality of types of nucleic acid fragments includes the following steps. An extracted genomic DNA is provided. The extracted genomic DNA is fragmented into a plurality of DNA fragments. A probe is hybridized to one of the DNA fragments. The hybridized probe is extended to form a labelled nascent strand-DNA fragment complex by using a DNA polymerase and labelled nucleotide analogs. The labelled nascent strand-DNA fragment complex is purified. A plurality of single-strand DNA fragments are eluted by dissociating the labelled nascent strand-DNA fragment complex. Adaptors are joined onto one end of the single-strand DNA fragments to form labelled single-strand DNA fragments.

In an embodiment of the invention, preparing the plurality of types of nucleic acid fragments further includes performing a washing process in the step of purifying the labelled nascent strand-DNA fragment complex.

Based on the above, the invention provides an apparatus for single molecule sequencing and a method of sequencing nucleic acid molecules, wherein the apparatus includes at least one nanowell, a plurality of nucleic acid immobilization moieties, and a plurality of types of nucleic acid fragments. In this method, although a plurality of types of nucleic acid fragments are added simultaneously, only one primer-polymerase-nucleic acid complex is formed at each moment, and only one nucleic acid fragment (indicated as single molecular) is sequenced at each moment. In some embodiments, after sequencing one type of nucleic acid fragment, the same type or another type of nucleic acid fragment is continuously sequenced, and the time for adding nucleic acid fragment to be sequenced between the two sequencing processes is saved. Accordingly, the apparatus and the method of present invention have the advantages of high throughput and reduced sample preparation time.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

FIG. 4A to FIG. 4G are schematic diagrams of a method for preparing a plurality of types of nucleic acid fragments in accordance with an embodiment of the present invention.

FIG. 5A to FIG. 5G are schematic diagrams of another method for preparing a plurality of types of nucleic acid fragments in accordance with an embodiment of the present invention.

DESCRIPTION OF THE EMBODIMENTS

The detailed description set forth below is intended as a description of the presently exemplary device provided in accordance with aspects of the present invention and is not intended to represent the only forms in which the present invention may be prepared or utilized. It is to be understood, rather, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described can be used in the practice or testing of the invention, the exemplary methods, devices and materials are now described.

Figure 1A:
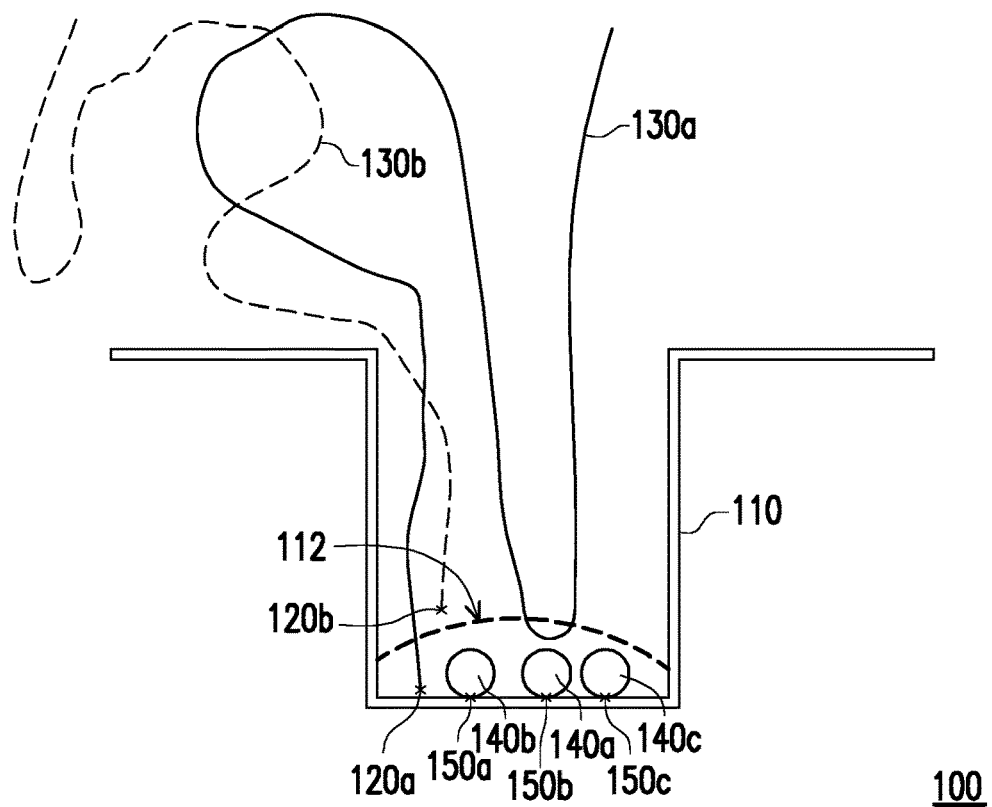
FIG. 1A to FIG. 1D is a schematic diagram of a method of sequencing nucleic acid molecules in accordance with an embodiment of the present invention.

FIG. 1A to FIG. 1D is a schematic diagram of a method of sequencing nucleic acid molecules in accordance with an embodiment of the present invention. FIG. 2 illustrates a flowchart of a method of sequencing nucleic acid molecules in accordance with an embodiment of the invention. Referring to FIG. 1A and FIG. 2 at the same time, first, in step S100, at least one nanowell 110 is provided, wherein the nanowell 110 has an observation zone 112. In some embodiments, an apparatus 100 including the nanowell 110 is provided, and the apparatus 100 is suitable for single molecule sequencing. In detail, the apparatus 100 includes the nanowell 110, a plurality of nucleic acid immobilization moieties 120a, 120b, a plurality of types of nucleic acid fragments 130a, 130b, and at least one polymerase 140a, 140b, 140c. In some embodiments, the apparatus 100 is suitable for sequencing a nucleic acid fragment having more than 200 nucleotides in length. It is noted that the number of the nucleic acid immobilization moieties, the nucleic acid fragments and the polymerase are exemplified for illustration purpose, and the invention is not limited thereof. In other words, the number of the nucleic acid immobilization moieties and the nucleic acid fragments may be respectively three or more, and the number of the polymerase may be 1 or more. It is noted that in some embodiments, the polymerase 140a, 140b, 140c are already in the apparatus 100, in some alternative embodiments, the polymerase can also be added later.

The nanowell 110 has an observation zone 112. In some embodiments, the observation zone 112 is formed at or near the bottom portion of nanowell 110. The bottom portion of nanowell 110 may be transparent, and thus the sequencing process in the nanowell 110 can be observed or detected via the observation zone 112. Accordingly, the observation zone 112 can be referred to as a detectable zone, sequencing site, or single molecule sequencing well. In some embodiments, a diameter of the observation zone 112 ranges from 10 nm to 500 nm, for example. In some embodiments, a height of the observation zone 112 is less than 200 nm, for example. In some embodiments, a height of the observation zone 112 is less than 100 nm, for example. In some embodiments, the upper boundary of the observation zone 112 may be in a curved shape.

Then, in step S110, a plurality of types of nucleic acid fragments 130a, 130b are immobilized to the observation zone 112 through a plurality of nucleic acid immobilization moieties 120a, 120b. The nucleic acid immobilization moieties 120a, 120b are disposed in or proximate to the observation zone 112. In some embodiments, the nucleic acid immobilization moiety 120a is disposed in the observation zone 112, and the nucleic acid immobilization moiety 120b is disposed proximate to the observation zone 112. The nucleic acid fragments 130a, 130b are templates to be sequenced, and are immobilized to the nucleic acid immobilization moieties 120a, 120b, respectively. The nucleic acid fragments 130a and 130b are different types of nucleic acid fragments, which means that the nucleic acid fragment 130a and the nucleic acid fragment 130b have different sequence. In some embodiments, the plurality of types of nucleic acid fragments 130a, 130b are linear. In some embodiments, the nucleic acid fragment may be a linear single stranded or a partially double stranded, such as a hairpin structure. In some embodiments, the nucleic acid fragments 130a, 130b include, for example, more than 200 nucleotides in length. In some alternative embodiments, the nucleic acid fragment has an immobilization anchor at 5' or 3' end, preferably at 3' end, and the nucleic acid fragment is immobilized to the nucleic acid immobilization moieties through the immobilization anchor. The immobilization anchor can also locate in other position of the nucleic acid fragment rather than the end.

The nucleic acid immobilization moieties 120a, 120b may be functional groups to immobilize the nucleic acid fragments 130a, 130b via covalent bonding or affinity binding. Exemplary functional groups for covalent bonding can be thiol, primary amine, secondary amine, diol, aldehyde, carboxyl group, methacrylate, methacrylate silane, aminosilane, mercaptosilane, aldehyde silane, diol silane, azidosilane, cysteine, cystine derivatives, amino-functional phosphonic acid and its derivatives, epoxy, maleimide, silane maleimide, silane PEG maleimide, or silane PEG azide, for example. Exemplary functional groups for affinity binding can be biotin, histidine, streptavidin, protein, protein inhibitor, protein substrate, antibody, antigen, or aptamer.

In some embodiments, the polymerases 140a, 140b, 140c are disposed in the observation zone 112. In some embodiments, the nucleic acid fragments 130a, 130b have a longer length and are not entirely disposed in the observation zone 112, and thus the polymerase-nucleic acid complex may be disposed outside the observation zone 112 if the polymerase 140d is not immobilized in the observation zone 112. Accordingly, the apparatus 100 further includes a plurality of polymerase immobilization moieties 150a, 150b, 150c in the observation zone 112 for immobilizing the polymerase 140a, 140b, 140c. In this way, the plurality of polymerases 140a, 140b, 140c are localized in the observation zone 112 by being immobilized to the polymerase immobilization moieties 150a, 150b, 150c, respectively, and thus the polymerase-nucleic acid complex is also localized in the observation zone 112. It is noted that the number of the polymerase immobilization moieties is exemplified for illustration purpose, and the invention is not limited thereof.

Figure 1B:
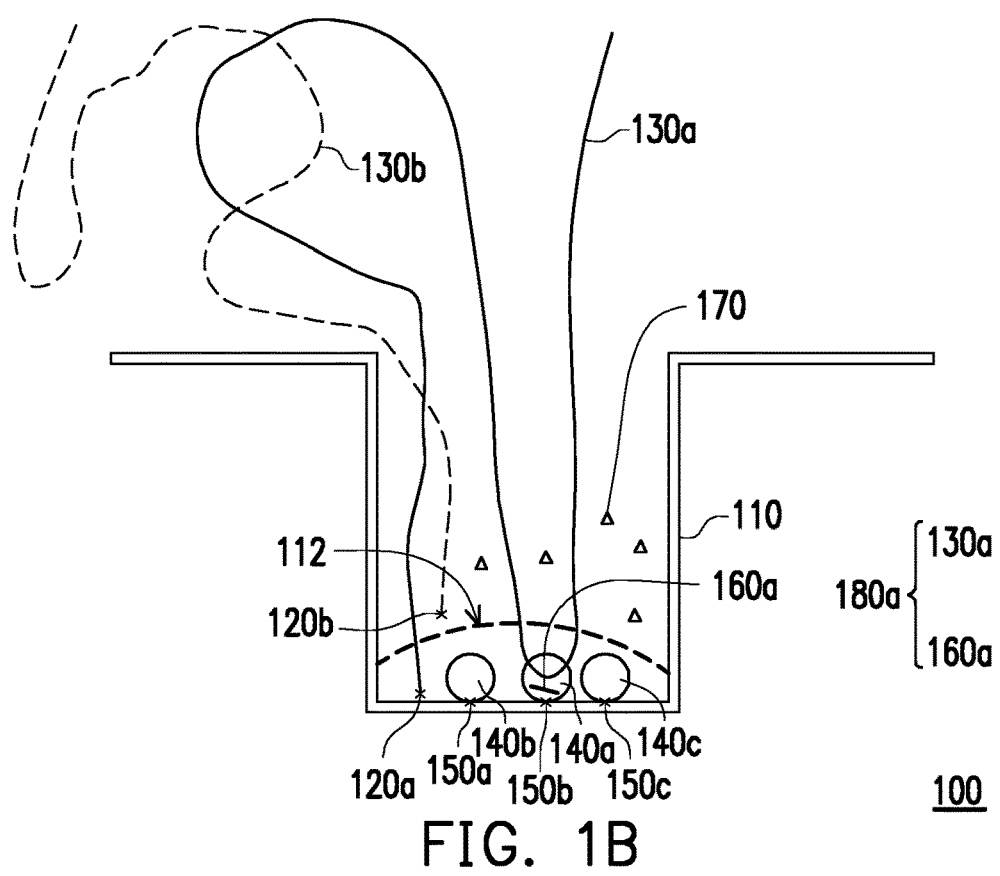
Figure 2:
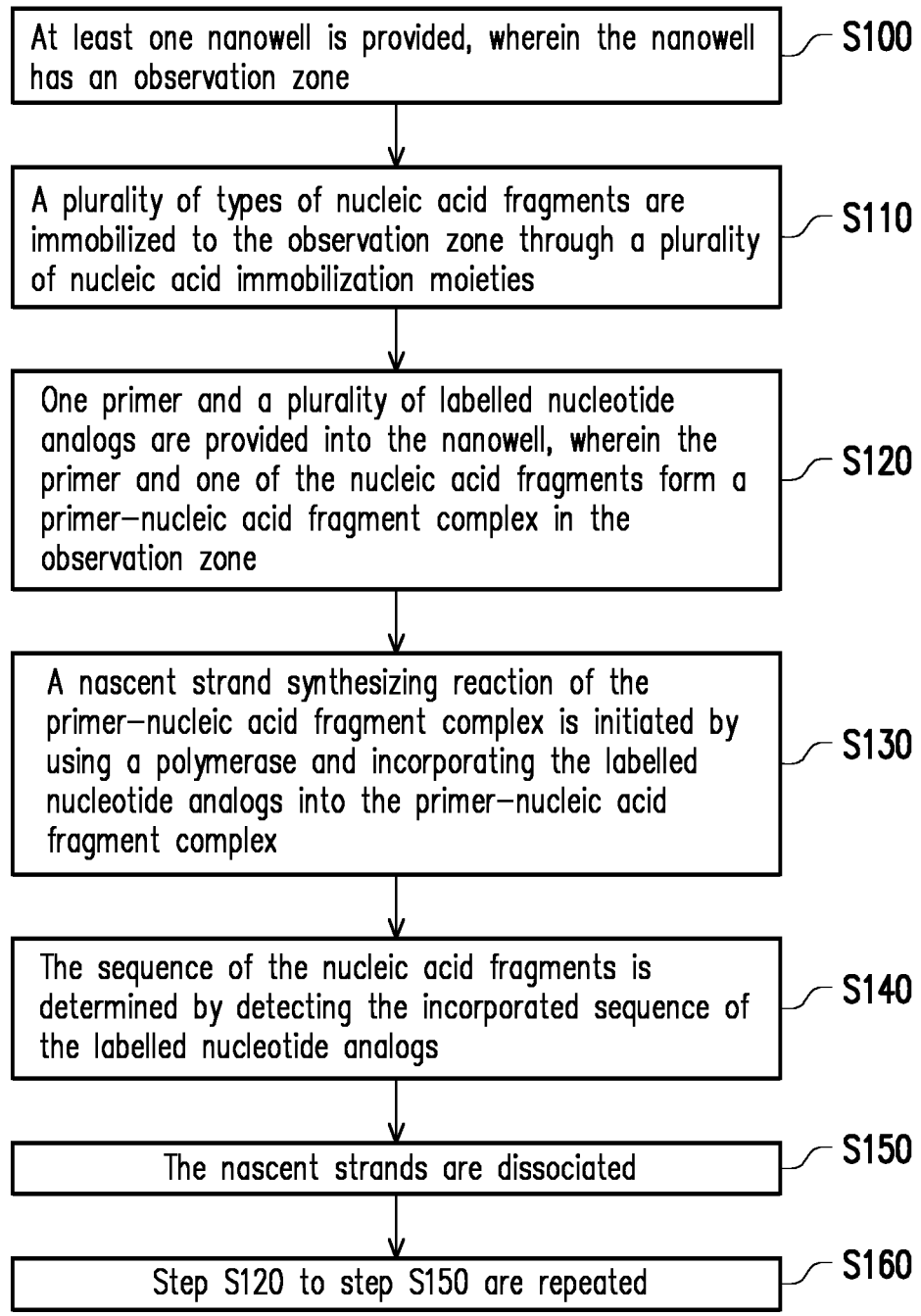
FIG. 2 illustrates a flowchart of a method of sequencing nucleic acid molecules in accordance with an embodiment of the invention.

Then, referring to FIG. 1B and FIG. 2 at the same time, in step S120, one primer 160a and a plurality of labelled nucleotide analogs 170 are provided into the at least one nanowell 110, wherein the primer 160a and one of the plurality of types of nucleic acid fragments 130a, 130b form a primer-nucleic acid fragment complex 180a in the observation zone 112. In some embodiments, only one primer 160a is added into the nanowell 110. In some embodiments, the primer 160a may have a sequence complement with the nucleic acid fragment 130a, and thus the primer 160a is annealed to the nucleic acid fragment 130a to form the primer-nucleic acid fragment complex 180a in the observation zone 112.

In some embodiments, the nucleic acid fragments 130a, 130b include, for example, more than 200 nucleotides in length. In some embodiments, the primer 160a may be annealed to a middle portion of the nucleic acid fragment 130a, so that the middle portion of the nucleic acid fragment 130a is a starting point for a sequencing process. However, the invention is not limited thereto. In some alternative embodiments, the sequencing process may start from the 5' end or anywhere to form a nascent strand via designed primers (probes) or via random priming of the nucleic acid fragment (not shown). In some embodiments, by adding only one primer, only one of the nucleic acid fragments 130a, 130b is primed for sequencing at a time. In some embodiments, the labelled nucleotide analogs 170 include labelled dATP, dCTP, dGTP and dTTP, for example. The labelled nucleotide analogs 170 may be fluorescently labelled nucleotide analogs.

Figure 1C:
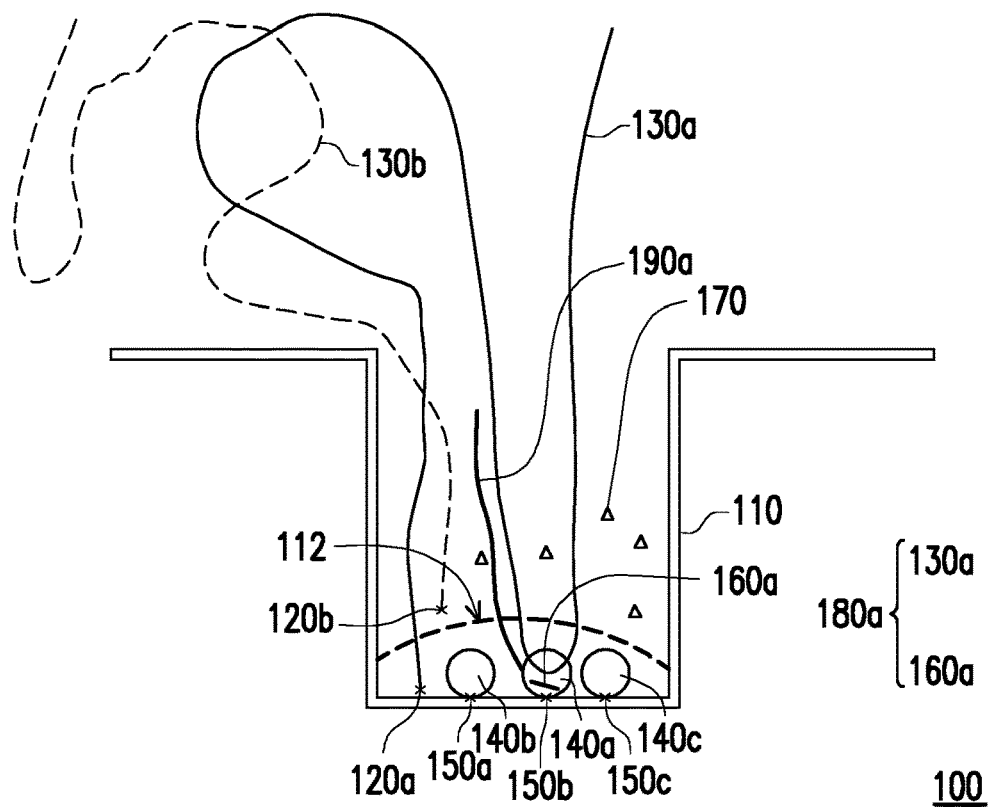

Thereafter, referring to FIG. 1C and FIG. 2 at the same time, in step S130, a nascent strand synthesizing reaction of the primer-nucleic acid fragment complex 180a is initiated by using a polymerase 140a, 140b, 140c and incorporating the plurality of labelled nucleotide analogs 170 into the primer-nucleic acid fragment complex 180a. In some embodiments, one of the polymerases 140a, 140b, 140c (for example, the polymerase 140a) is used to synthesize a nascent strand 190a. In some embodiments, the single molecule sequencing-by-synthesis process is initiated after forming the primer-polymerase-nucleic acid complex containing one of the nucleic acid fragments 130a, 130b, one of the polymerase 140a, 140b, 140c, and one primer 160a. That is, the starting point of the sequencing process is in the primer-polymerase-nucleic acid complex, and the sequencing process is initiated in the primer-polymerase-nucleic acid complex to synthesize a nascent strand 190a. It is noted that although steps S110, S120 and S130 are described sequentially, these steps simultaneously occur once the primer and the nucleotide analogs are added since the nucleic acid fragment and the polymerase are already added in the nanowell.

Then, in step S140, the sequence of the nucleic acid fragment 130a is determined by detecting the incorporated sequence of the labelled nucleotide analogs 170. In some embodiments, since only one labelled nucleotide analog 170 is incorporated into the primer-nucleic acid fragment complex 180a in the observation zone 112 at each moment, the sequence of the nucleic acid fragment 130a may be determined with a high accuracy. In some embodiments, the labelled nucleotide analogs 170 include labelled dATP, dCTP, dGTP and dTTP with different fluorescent, respectively. In some embodiments, the sequence of the nucleic acid fragment 130a can be determined by detecting the different fluorescent signals of incorporated sequence of the labelled dATP, dCTP, dGTP and dTTP.

After that, in step S150, the nascent strand 190a is dissociated. In some embodiments, the sequencing process by synthesizing the nascent strand 190a might be terminated due to loss activity of polymerase 140a or release of the nucleic acid fragment 130a. However, after dissociating the nascent strand 190a, the sequencing process can be recovered by re-capturing the polymerase 140a, 140b, 140c nearby. Specifically, if the sequencing process is terminated due to loss of polymerase 140a activity, the polymerase 140a can be removed optionally and another polymerase 140b, 140c nearby can be re-captured to recover the sequencing process. If the sequencing process is terminated due to release of the nucleic acid fragment 130a, the same polymerase 140a or another polymerase 140b, 140c nearby can be re-captured to recover the sequencing process.

Figure 1D:
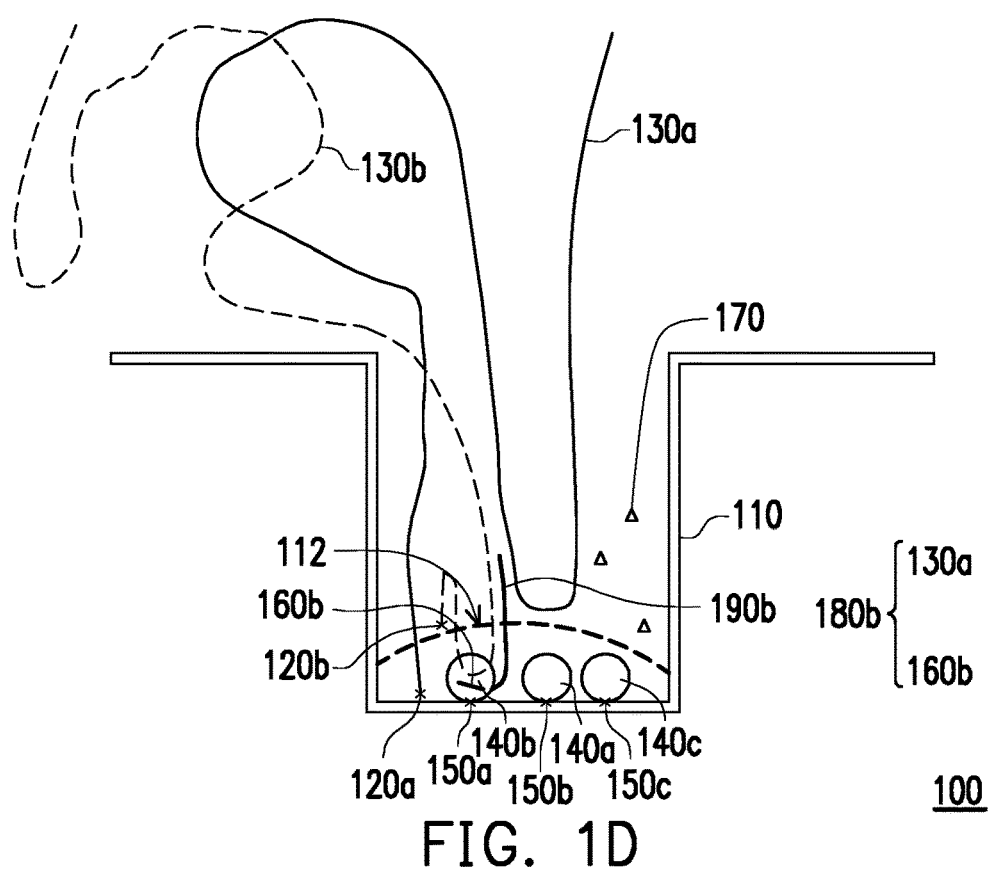

Thereafter, referring to FIG. 1D and FIG. 2 at the same time, in step S160, step S120 to step S150 are repeated. In some embodiments, in repeated step S120, a new primer 160b is added and one of the polymerases 140a, 140b, 140c is re-captured to synthesize a nascent strand 190b. In some embodiments, the polymerases 140b is only used for the purpose of illustration. In other words, as mentioned above, in some alternative embodiments, in repeated step S130, the polymerase 140a or another polymerase 140c may be re-captured to synthesize the nascent strand 190a. Accordingly, the sequencing process can be repeated several times by dissociating the nascent strand, providing new primer and recapturing one of the polymerases. In some embodiments, step S120 to step S150 are repeated to increase the sequence coverage of the nucleic acid fragments 130a, 130b until necessary accuracy of consensus sequence is reached. It is noted that since the polymerases 140a, 140b, 140c exist in the nanowell from the beginning, the addition of the primer initiates the single molecule sequencing-by-synthesis process. It is noted that in some embodiments, although the nucleic acid fragment 130b is immobilized proximate to the observation zone 112, the primer-polymerase-nucleic acid complex of the nucleic acid fragments 130b, primer 160b and the polymerases 140b can be formed and localized in the observation zone 112. In other words, "proximate" means the nucleic acid fragment 130b is close to the observation zone 112, and the nucleic acid fragment 130b and the observation zone 112 are separated by a distance, wherein the distance is suitable for the nucleic acid fragments 130b to form the primer-polymerase-nucleic acid complex in the observation zone 112. For single stranded DNA molecule, the average length per base is about 0.6 to 0.7 nm (The persistence length and length per base of single-stranded DNA are obtained from fluorescence correlation spectroscopy measurements using mean field theory, Physica A: Statistical Mechanics and its Applications Volume 392, Issue 5, 1 Mar. 2013, Pages 1072-1079). As some of the nucleic acid fragment 130b is not fully immobilized inside the observation zone, but part of the fragment is long enough to diffuse into the observation zone and form a primer-polymerase-nucleic acid complex with the polymerase that immobilized inside the observation zone, thereby the sequencing process can be proceeded. In some embodiments, the distance from the border of the observation zone 112 to the nucleic acid immobilization moiety 120b of nucleic acid fragment 130b must be within L×0.6×50% nm in order to effectively form the primer-polymerase-nucleic acid complex in the observation zone 112 from the border of the observation zone to the immobilization point, for example, where L is the fragment length in bases.

In some embodiments, the nucleic acid fragments 130a, 130b are immobilized in or proximate to the same observation zone 112, so that the nucleic acid fragments 130a, 130b can be sequenced alternately and completely in the same observation zone 112 without cleaning up and reloading another nucleic acid fragments. In other words, after sequencing one type of nucleic acid fragment 130a, the same type of nucleic acid fragment 130a or another type of nucleic acid fragment 130b can be continuously sequenced since the nucleic acid fragments 130a, 130b already exist in the nanowell, and the time for adding the nucleic acid fragments to be sequenced between the two sequencing processes is saved. In some embodiments, after sequencing one nucleic acid fragment 130a, the same nucleic acid fragment 130a or another nucleic acid fragment 130b can be continuously sequenced since the nucleic acid fragments 130a, 130b already exist in the nanowell, and the time for adding the nucleic acid fragments to be sequenced between the two sequencing processes is saved. It is noted that although the nucleic acid fragments 130a, 130b are immobilized in or proximate to the same observation zone 112 simultaneously, only one primer-polymerase-nucleic acid complex is formed at each moment, and only one nucleic acid fragment (indicated as single molecular) 130a is sequenced at each moment.

Figure 3:
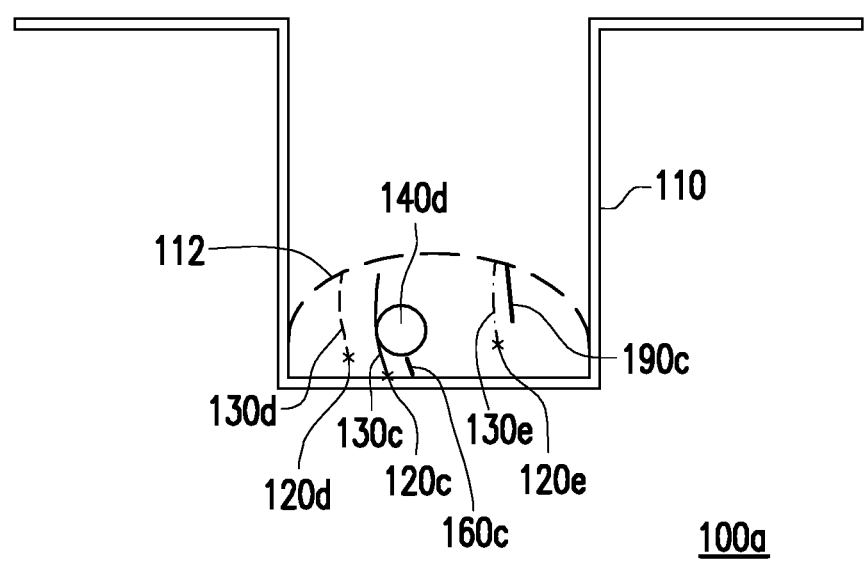
FIG. 3 is a schematic diagram of an apparatus suitable for single molecule sequencing in accordance with an embodiment of the present invention.

It is noted that although the nucleic acid fragments 130a, 130b include, for example, more than 200 nucleotides in length in FIG. 1A to FIG. 1D, the invention is not limited thereto. In some embodiments, as shown in FIG. 3, the nucleic acid fragments 130c, 130d, 130e include, for example, 50 nucleotides to 200 nucleotides in length. In some embodiments, the nucleic acid fragments 130c, 130d, 130e are short fragments such as cell free DNA or micro RNA. In some embodiments, the nucleic acid fragments 130c, 130d, 130e are immobilized to the nucleic acid immobilization moieties 120c, 120d, 120e, respectively. Since the nucleic acid fragments 130c, 130d, 130e have a shorter length, the nucleic acid fragments 130c, 130d, 130e are substantially entirely disposed in or proximate to the observation zone 112. Accordingly, there is no need to immobilize the polymerase 140d in the observation zone 112. In addition, in some embodiments, the addition of one primer 160c and one polymerase 140d into the nanowell 110 initiates the formation of the primer-polymerase-nucleic acid complex and performing the single molecule sequencing-by-synthesis process. In some embodiments, the sequencing process by synthesizing the nascent strand 190c might be terminated due to loss of polymerase 140d activity or release of the nucleic acid fragment 130e. However, after dissociating the nascent strand 190c, the sequencing process can be recovered by re-capturing another newly added polymerase (not shown). Specifically, if the sequencing process is terminated due to loss of polymerase 140d activity, the polymerase 140d can be removed optionally and newly added polymerase (not shown) can be re-captured to recover the sequencing process. If the sequencing process is terminated due to release of the nucleic acid fragment 130e, the same polymerase 140d can be re-captured to recover the sequencing process. It is noted that although three nucleic acid fragments 130c, 130d, 130e are schematically illustrated in FIG. 3, the invention is not limited thereto. In some alternative embodiments, the nucleic acid fragments may also be tens, even hundreds of fragments at one loading and each fragment can be repeatedly sequenced. Therefore, the sequencing capacity of the apparatus 100a can be multiply increased.

FIG. 3 is a schematic diagram of an apparatus suitable for single molecule sequencing in accordance with an embodiment of the present invention. The components of the apparatus 100a are similar to those of the apparatus 100, and the main difference between the apparatuses 100, 100a lies in that the apparatus 100 is suitable for sequencing a longer nucleic acid fragment (such as having more than 200 nucleotides in length) and the apparatus 100a lies is suitable for sequencing a shorter nucleic acid fragment (such as having less than 200 nucleotides in length). The difference is described below. Referring to FIG. 3, the apparatus 100a includes at least one nanowell 110, a plurality of nucleic acid immobilization moieties 120c, 120d, 120e (for the purpose of illustration, three nucleic acid immobilization moieties 120c, 120d, 120e are schematically illustrated in FIG. 3), a plurality of types of nucleic acid fragments 130c, 130d, 130e (for the purpose of illustration, three types of nucleic acid fragments 130c, 130d, 130e are schematically illustrated in FIG. 3), and only one polymerase 140d. Here, the nucleic acid fragments 130c, 130d, 130e include, for example, 50 nucleotides to 200 nucleotides in length. The nucleic acid fragments 130c, 130d and 130e are different types of nucleic acid fragments, which means that the nucleic acid fragment 130c, the nucleic acid fragment 130d, and the nucleic acid fragment 130e have different sequence. In some embodiments, the polymerase 140d is disposed in the observation zone 112. In some embodiments, the nucleic acid fragments 130c, 130d, 130e have a shorter length and are entirely disposed in or proximate to the observation zone 112, and thus the primer-polymerase-nucleic acid complex may be localized in the observation zone 112. In some embodiments, the primer-polymerase-nucleic acid complex is a complex containing one primer, one polymerase and one nucleic acid fragment. Therefore, the polymerase 140d is not required to be additionally immobilized in the observation zone 112.

Briefly, in the apparatus for single molecule sequencing, the plurality of nucleic acid immobilization moieties are disposed in or proximate to the observation zone of the nanowell, and the plurality of types of nucleic acid fragments are immobilized to the nucleic acid immobilization moieties. Although a plurality of types of nucleic acid fragments are added simultaneously in the nanowell, only one primer-polymerase-nucleic acid complex is formed at each moment, and only one type of nucleic acid fragment (indicated as single molecular) is sequenced at each moment. In addition, after sequencing one type of nucleic acid fragment, the same type or another type of nucleic acid fragment is continuously sequenced since it already exists in the nanowell, and the time for adding nucleic acid fragments to be sequenced between the two sequencing processes is saved. Accordingly, the apparatus and the method of present invention have the advantages of high throughput and reduced sample preparation time.

FIG. 4A to FIG. 4G are schematic diagrams of a method for preparing a plurality of types of nucleic acid fragments in an embodiment of the present invention. FIG. 5A to FIG. 5G are schematic diagrams of another method for preparing a plurality of types of nucleic acid fragments in another embodiment of the present invention.

Referring to FIG. 4A to FIG. 4G, a method for preparing the plurality of types of nucleic acid fragments includes the following steps. First, an extracted genomic DNA 210 is provided. Then, the extracted genomic DNA 210 is fragmented into a plurality of DNA fragments 212. After that, one end 212a of the DNA fragments 212 is joined onto dsDNA adaptors 220, wherein the dsDNA adaptors 220 are immobilized on a solid phase 230. Thereafter, a washing process is performed to wash away unbound DNA fragments 212. Then, labelled adaptors 240 are joined onto the other end 212b of the DNA fragments 212 attached on the solid phase 230 to form labelled DNA fragments 214. In some embodiments, the labelled adaptors 240, for example, are partially double stranded DNA with a single stranded portion, wherein a label F is labelled on the end of the single stranded portion. In some embodiments, the label F is biotin, for example. After that, a washing process is performed to wash away unattached labelled adaptors 240. Thereafter, a plurality of single-strand DNA fragments 214a are eluted by dissociating the labelled DNA fragments 214. Here, the single-strand DNA fragments 214a may be directly used as the nucleic acid fragments for sequencing.

Referring to FIG. 5A to FIG. 5G, another method for preparing the plurality of types of nucleic acid fragments includes the following steps. First, an extracted genomic DNA 310 is provided. Then, the extracted genomic DNA 310 is fragmented into a plurality of DNA fragments 312. After that, a probe 320 is hybridized to one of the DNA fragments 312. Thereafter, the hybridized probes 322 are extended to form a labelled nascent strand-DNA fragment complex 313 by using DNA polymerase 330 and labelled nucleotide analogs 340. In some embodiments, each of the labelled nucleotide analogs 340 contain a label, and the label is biotin, for example. Then, the labelled nascent strand-DNA fragment complex 313 is purified. A washing process is performed to wash away unlabelled DNA fragments 312. In some embodiments, the labelled nascent strand-DNA fragment complex 313 is purified by streptavidin-coated magnetic beads 350 and a magnet 360. After that, a plurality of single-strand DNA fragments 313a are eluted by dissociating the labelled nascent strand-DNA fragment complex 313. Thereafter, anchors 370 are joined onto one end 313a1 (or the other end 313a2) of the single-strand DNA fragments 313a to form labelled single-strand DNA fragments 314. Here, the labelled single-strand DNA fragments 314 may be directly used as the nucleic acid fragments for sequencing.

In some embodiments, each sequencing process may result in a partial sequence of the nucleic acid fragments. The partial sequence can start from a same starting point or from different starting points, and end at different end points. The sequencing process can be repeated several times to obtain several partial sequences in one nanowell. Then, by aligning the several partial sequences together, longer consensus sequence of the nucleic acid fragment can be obtained.

To sum up, the invention provides an apparatus for single molecule sequencing and a method of sequencing nucleic acid molecules, and the apparatus includes at least one nanowell, a plurality of nucleic acid immobilization moieties, and a plurality of types of nucleic acid fragments. In some embodiments, the initiation of the sequencing process can be controlled by addition of one primer or one polymerase, and thus it ensures there is only one primer-polymerase-nucleic acid complex formed. Accordingly, at each moment, only one labelled nucleotide analog is incorporated into the primer-polymerase-nucleic acid complex, and this labelled nucleotide analog can be detected as a sequencing result through the observation zone of the nanowell. Therefore, the sequencing result can be obtained accurately without interference. In addition, the nucleic acid fragments can be sequenced continuously and the time to add the nucleic acid fragments to be sequenced is saved since they are added to the nanowell from the beginning. Moreover, since the loading number of the nucleic acid fragments and/or the polymerases in one nanowell is increased (large than 1) at one loading, the failure loading can be prevented. Accordingly, the apparatus and the method of present invention have the advantages of high throughput and reduced sample preparation time.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method of sequencing nucleic acid molecules comprising:
   (a) providing at least one nanowell, wherein the at least one nanowell has an observation zone;

(b) immobilizing a plurality of types of nucleic acid fragments to the observation zone through a plurality of nucleic acid immobilization moieties;

(c) providing only one primer and a plurality of labelled nucleotide analogs into the at least one nanowell, wherein the only one primer and one of the plurality of types of nucleic acid fragments form a primer-nucleic acid fragment complex in the observation zone;

(d) forming a nascent strand by initiating a nascent strand synthesizing reaction of the primer-nucleic acid fragment complex through using a polymerase and incorporating the plurality of labelled nucleotide analogs into the primer-nucleic acid fragment complex;

(e) determining the sequence of one of the plurality of types of the nucleic acid fragments by detecting the incorporated sequence of the plurality of labelled nucleotide analogs;

(f) dissociating the nascent strand; and (g) repeating step (c) to step (f).

2. The method as claimed in claim 1, wherein the diameter of the observation zone is between 10 nm to 500 nm, and the height of the observation zone is less than 200 nm.

3. The method as claimed in claim 1, wherein the plurality of types of nucleic acid fragments comprise 50 nucleotides to 200 nucleotides in length.

4. The method as claimed in claim 3, wherein step (c) further comprises adding the polymerase.

5. The method as claimed in claim 1, wherein the plurality of types of nucleic acid fragments comprise more than 200 nucleotides in length.

6. The method as claimed in claim 5, further comprising immobilizing a plurality of polymerases to the observation zone through a plurality of polymerase immobilization moieties, wherein the polymerase used in step (d) is one of the plurality of polymerases.

7. The method as claimed in claim 6, wherein the step of immobilizing the plurality of polymerases is performed before step (c).

8. The method as claimed in claim 6,
wherein the polymerase used in repeated step (d) is one of the plurality of polymerases.

9. The method as claimed in claim 1, wherein a preparing method of the plurality of types of nucleic acid fragments comprises:

providing an extracted genomic DNA;

fragmenting the extracted genomic DNA into a plurality of DNA fragments;

joining one end of the DNA fragments onto dsDNA adaptors, wherein the dsDNA adaptors are immobilized on a solid phase;

joining labelled adaptors onto the other end of the DNA fragments to form labelled DNA fragments; and eluting a plurality of single-strand DNA fragments by dissociating the labelled DNA fragments.

10. The method as claimed in claim 9, before joining the labelled adaptors and before eluting the plurality of single-strand DNA fragments, further comprising performing a washing process respectively.

11. The method as claimed in claim 1, wherein a preparing method of the plurality of types of nucleic acid fragments comprises:

providing an extracted genomic DNA;

fragmenting the extracted genomic DNA into a plurality of DNA fragments;

hybridizing a probe to one of the DNA fragments;

extending the hybridized probe to form a labelled nascent strand-DNA fragment complex by using a DNA polymerase and labelled nucleotide analogs;

purifying the labelled nascent strand-DNA fragment complex; and eluting a plurality of single-strand DNA fragments by dissociating the labelled nascent strand-DNA fragment complex.

12. The method as claimed in claim 11, further comprising performing a washing process in the step of purifying the labelled nascent strand-DNA fragment complex.

13. The method as claimed in claim 11, wherein immobilizing the plurality of types of nucleic acid fragments to the observation zone through the plurality of nucleic acid immobilization moieties comprises:

joining anchors onto one end of the plurality of single-strand DNA fragments to form labelled single-strand DNA fragments with the anchors; and immobilizing the labelled single-strand DNA fragments to the nucleic acid immobilization moieties through the anchors.

* * * * *